(12) United States Patent
Tiwald

(10) Patent No.: US 7,636,161 B1
(45) Date of Patent: *Dec. 22, 2009

(54) BACK SURFACE REFLECTION REDUCTION SYSTEMS AND METHODOLOGY

(75) Inventor: Thomas E. Tiwald, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 400 days.

This patent is subject to a terminal disclaimer.

(21) Appl. No.: 11/725,603

(22) Filed: Mar. 20, 2007

Related U.S. Application Data

(63) Continuation-in-part of application No. 11/452,483, filed on Jun. 14, 2006.

(60) Provisional application No. 60/691,297, filed on Jun. 17, 2005, provisional application No. 60/790,588, filed on Apr. 10, 2006.

(51) Int. Cl.
  *G01J 4/00* (2006.01)
(52) U.S. Cl. ...................................... 356/369
(58) Field of Classification Search ................. 356/369
  See application file for complete search history.

(56) References Cited

U.S. PATENT DOCUMENTS

| | | | |
|---|---|---|---|
| 4,838,695 A * | 6/1989 | Mansuripur et al. ......... 356/369 |
| 4,934,818 A * | 6/1990 | Glantschnig et al. ....... 356/73.1 |
| 5,108,185 A * | 4/1992 | Mansuripur et al. ......... 356/369 |
| 5,171,995 A * | 12/1992 | Gast et al. ............. 250/339.08 |
| 5,208,648 A * | 5/1993 | Batchelder et al. ....... 356/237.1 |
| 5,220,403 A * | 6/1993 | Batchelder et al. .......... 356/450 |
| 5,442,443 A * | 8/1995 | Guerra ....................... 356/600 |
| 5,608,526 A | 3/1997 | Piwonka-Corle et al. .... 356/369 |
| 5,852,494 A * | 12/1998 | Skladnev et al. ......... 356/243.1 |
| 5,903,352 A * | 5/1999 | Ohsaki et al. ............... 356/364 |
| 5,910,842 A | 6/1999 | Piwonka-Corle et al. .... 356/369 |
| 5,917,594 A | 6/1999 | Norton ...................... 356/327 |
| 5,929,993 A | 7/1999 | Johs ........................... 356/364 |
| 5,936,734 A | 8/1999 | Johs et al. ................... 356/364 |
| 5,963,327 A | 10/1999 | He et al. ..................... 356/369 |
| 6,323,946 B1 | 11/2001 | Norton ....................... 356/327 |
| 6,455,853 B2 | 9/2002 | Herzinger et al. ........ 250/341.4 |
| 6,583,877 B2 | 6/2003 | Norton ....................... 356/369 |
| 6,734,967 B1 | 5/2004 | Piwonka-Corle et al. .... 356/369 |
| 6,738,139 B1 | 5/2004 | Synowicki et al. .......... 356/369 |
| 2002/0030813 A1 | 3/2002 | Norton | |
| 2004/0008349 A1 | 1/2004 | Norton | |
| 2004/0100632 A1 | 5/2004 | Piwonka-Corle et al. | |
| 2005/0105090 A1 | 5/2005 | Piwonka-Corle et al. | |

* cited by examiner

*Primary Examiner*—Roy Punnoose
(74) *Attorney, Agent, or Firm*—James D. Welch

(57) ABSTRACT

A system for reducing reflections of a beam of electromagnetic from the back of a sample, including methodology of use.

20 Claims, 2 Drawing Sheets

BACK SURFACE REFLECTION REDUCTION SYSTEMS AND METHODOLOGY

This Application is a CIP of application Ser. No. 11/452,483 Filed Jun. 14, 2006, and therevia claims Benefit from Provisional Application Ser. No. 60/691,297 Filed Jun. 17, 2005; and further claims Benefit of Provisional Application Ser. 60/790,588 Filed Apr. 10, 2006.

TECHNICAL FIELD

The present invention relates to reduction of reflections of a beam of electromagnetic from the back of a sample upon which it is incident at an oblique or normal angle, and especially to system and methodology for reducing such back reflections from continuously moving samples.

BACKGROUND

It is known that when a beam of electromagnetic radiation is caused to impinge on the surface of a sample at an oblique or normal angle, reflected electromagnetic radiation from said sample generally contains components not only from its surface, but also from the backside thereof. The effect of said backside reflections can be difficult to model, and makes characterization of surface films far more difficult, even essentially impossible. It is therefore desirable to reduce or eliminate the presence of said backside reflections. It is disclosed that the identified problem can present in systems where a sample is elongated such as a ribbon or sheet, and is continuously pulled over the means for supporting a sample. Where said sample and means for supporting it have different refractive indicies, back side reflections develop.

Known Patents relevant to Backside Reflections are:
Patent to He et al., U.S. Pat. No. 5,963,327;
Patent to Johs, U.S. Pat. No. 5,929,993;
Patent to Synowicki, U.S. Pat. No. 6,738,139;
Patent to Johs et al. U.S. Pat. No. 5,936,734;
Patent to Herzinger et al. U.S. Pat. No. 6,455,853.

Other Patents and Published Applications which were cited in Parent application Ser. No. 11/452,483 are:
U.S. Pat. No. 5,917,594;
U.S. Pat. No. 6,323,946;
U.S. Pat. No. 6,583,877;
U.S. Pat. No. 5,608,526;
U.S. Pat. No. 5,910,842;
U.S. Pat. No. 6,734,967;
Patent Application No. US 2002/030813;
Patent Application No. US 2004/008349;
Patent Application No. US 2004/100632;
Patent Application No. US 2005/105090.

Need remains for systems which reduce the effect of reflections for the backside of a sample when electromagnetic radiation is caused to impinge on a front side thereof at an oblique or normal angle of incidence.

DISCLOSURE OF THE INVENTION

The present invention provides an approach to investigation of samples which reduces the effect of back reflections. A system for accomplishing this comprises:
a sample;
a means for supporting said sample;
a source of a beam of electromagnetic radiation; and
a detector of electromagnetic radiation.

Said means for supporting a sample is present under said sample near the location thereof whereat, during use, a beam of electromagnetic radiation provided by said source thereof is caused to impinge thereupon at an oblique or normal angle of incidence, and reflect into said detector. Said means for supporting a sample and said sample can be characterized by a selection from the group consisting of:
having substantially matched indices of refraction; and
having liquid present at the interface therebetween which is substantially index matched to that of said sample.

Said sample and said means for supporting a sample can be variously rigid or flexible, and an important application of the present invention system is where relative motion therebetween is continuous. This can occur, for instance, where the sample is a ribbon or sheet which is continuously pulled over the means for supporting a sample. In such a case, said means for supporting a sample can be a roller characterized by a selection from the group consisting of:
it is rigid; and
it is deformable.

For instance, where a sample is rigid, benefit derives from using a deformable means for supporting a sample in order to facilitate effecting a good contact therebetween. This point is less important, though not irrelevant however, where the sample is flexible and can conform to the shape of said means for supporting a sample, and/or in the case where liquid is caused to be present between said sample and said means for supporting a sample.

It is noted that index matching need not be perfect to achieve beneficial results.

A method of monitoring reflections of electromagnetic radiation caused to impinge on the surface of a sample at an oblique or normal angle of incidence, while substantially preventing backside reflections therefrom from complicating the results, comprises the steps of:
a) providing a system comprising:
a sample;
a means for supporting said sample;
a source of a beam of electromagnetic radiation; and
a detector of electromagnetic radiation;

wherein said means for supporting a sample is present under said sample near the location of said sample whereat, during use, a beam of electromagnetic radiation provided by said source of a beam of electromagnetic radiation is caused to impinge at an oblique or normal angle of incidence, reflect therefrom, and enter said detector of electromagnetic radiation;

said means for supporting a sample and said sample being characterized by a selection from the group consisting of:
having substantially matched indices of refraction; and
having liquid present at the interface therebetween which is substantially index matched to that of said sample;
b) causing said source of a beam of electromagnetic radiation to provide a beam of electromagnetic radiation which impinges on a surface of said sample, at an oblique or normal angle of incidence;
c) monitoring electromagnetic radiation reflected from said sample surface which enters said detector of electromagnetic radiation.

(Note, the means for supporting a sample will typically contact a lower surface of a sample at a location thereof which is substantially directly below where a beam of electromagnetic radiation is caused to impinge upon a top surface of said sample in step b).

Said method can be further characterized by at least one selection from the group consisting of:

storing at least some data provided by said data detector of electromagnetic radiation in machine readable media;

analyzing at least some of the data provided by said data detector of electromagnetic radiation and storing at least some of the results of said analysis in machine readable media;

displaying at least some data provided by said data detector of electromagnetic radiation by electronic and/or non-electronic means;

analyzing at least some of the data provided by said data detector of electromagnetic radiation and displaying at least some of the results of said analysis by electronic and/or non-electronic means;

causing at least some data provided by said data detector of electromagnetic radiation to produce a signal which is applied to provide a concrete and tangible result;

analyzing at least some of the data provided by said data detector of electromagnetic radiation and causing at least some thereof to produce a signal which is applied to provide a concrete and tangible result.

It is also noted that if the sample is elongated, the beam of electromagnetic radiation provided by said source thereof which is caused to impinge thereupon at an oblique or normal angle of incidence; can be directed along a locus which is selected from the group consisting of:

parallel to the elongated dimension of said sample;

perpendicular to the elongated dimension of said sample;

between parallel and perpendicular to the elongated dimension of said sample.

It is to be appreciated that a Sample (SM) can be supported in a way that does not place a solid means for supporting (R) directly thereunder, such as a split system that supports the Sample (SM) on either side of a position at which the Beam (EMI) impinges. In that case the index matching is to the atmosphere under the Sample (SM). Such a situation is to be considered to be within the scope of the claims.

The present invention will be better understood by reference to the Detailed description Section of this Application, in combination with the Drawings.

SUMMARY OF THE INVENTION

It is a purpose and/or objective of the present invention to apply the system of the present invention to investigate a sample which is supported by a means for supporting a sample, said sample and means for supporting it being characterized by a selection from the group consisting of:

they have substantially matched indices of refraction; and they have liquid present at the interface therebetween which is substantially index matched to that of said sample.

Another purpose and/or objective of the present invention is to apply the system of the present invention to investigate a sample which is of an elongated sheet or ribbon shape, which sample is supported by a means for supporting a sample at a location on said sample which is substantially directly below where a beam of electromagnetic radiation is caused to impinge upon a top surface of said sample, as said sample is caused to be slid over said means for supporting it.

Other purposes and/or objectives of the present invention will become apparent by a reading of the Specification and claims.

DETAILED DESCRIPTION

Turning now to the Drawings, FIGS. 1-4 demonstrate samples (SM) which can be investigated by the present invention system, including means to reduce back side reflections. The system generally comprises a Source (S) and Detector (D) as a unit, and a Sample (SM). The systems in FIGS. 1-4 is further show that:

said sample (SM) has top (S1) and bottom (S2) surfaces; and there is a means for supporting (R) said sample (SM), said means for supporting (R), having an outer surface (S3); and said source (PSG) is shown as a polarization state generator of a beam of electromagnetic radiation (EMI) and said detector (PSD) is shown as being a polarization state detector and as receiving of a reflected beam of electromagnetic radiation (EMR).

Importantly, note that a portion of the beam (EMI) transits into the sample as (EMT), and can reflect from an interface between said sample (SM) and said means for supporting (R) said Sample (SM). Said means for supporting (R) a sample (SM) is present under said sample (SM) near the location thereof whereat, during use, a beam of electromagnetic radiation (EMI) provided by said source thereof is caused to impinge thereupon at an oblique or normal angle of incidence. Also note that said means for supporting (R) a sample (SM) and said sample (SM) are characterized by a selection from the group consisting of:

having substantially matched indices of refraction, (FIGS. 1 and 2); and having liquid (L), (FIGS. 3 and 4), present at the interface therebetween which is substantially index matched to that of said sample (SM).

Figure 1:
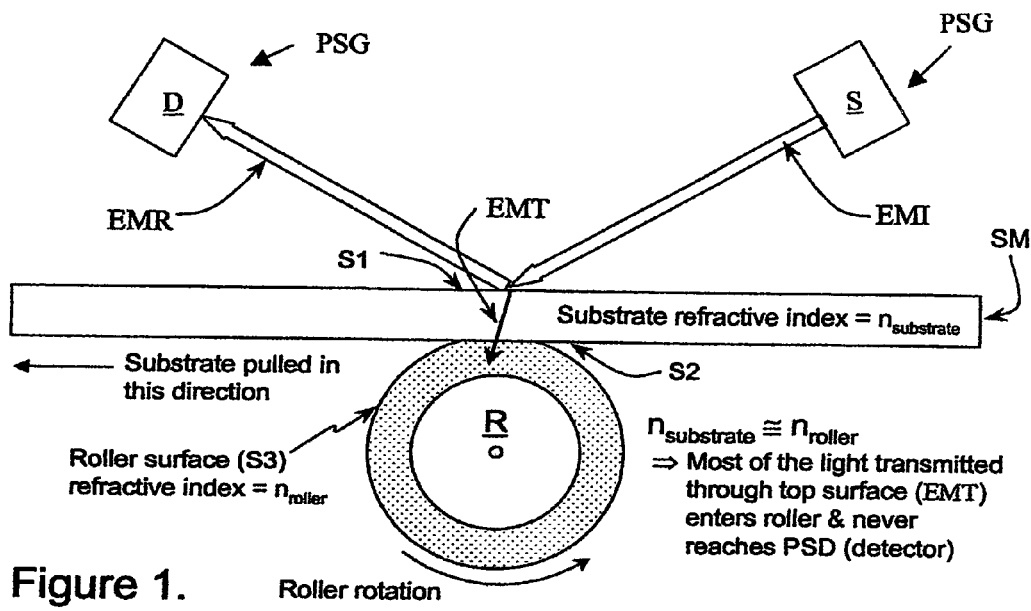
FIGS. 1 and 2 demonstrate present invention systems components for supporting a sample, including means to reduce back side reflections, in combination with samples in place therewith, said samples and components for supporting them being substantially index matched such that backside reflections are reduced when the samples are investigated by thereby.
Figure 2:
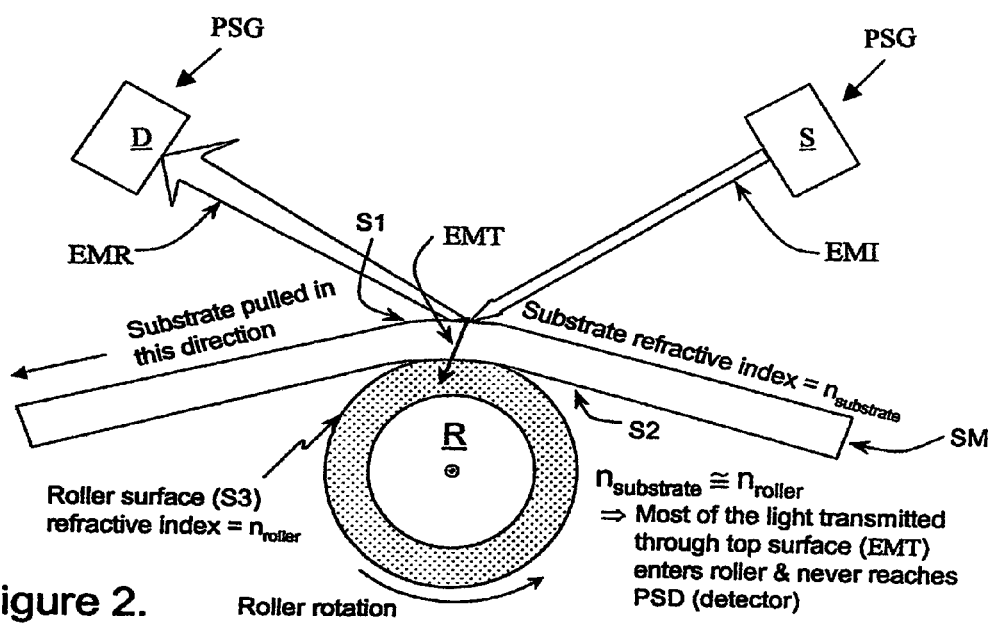
Figure 3:
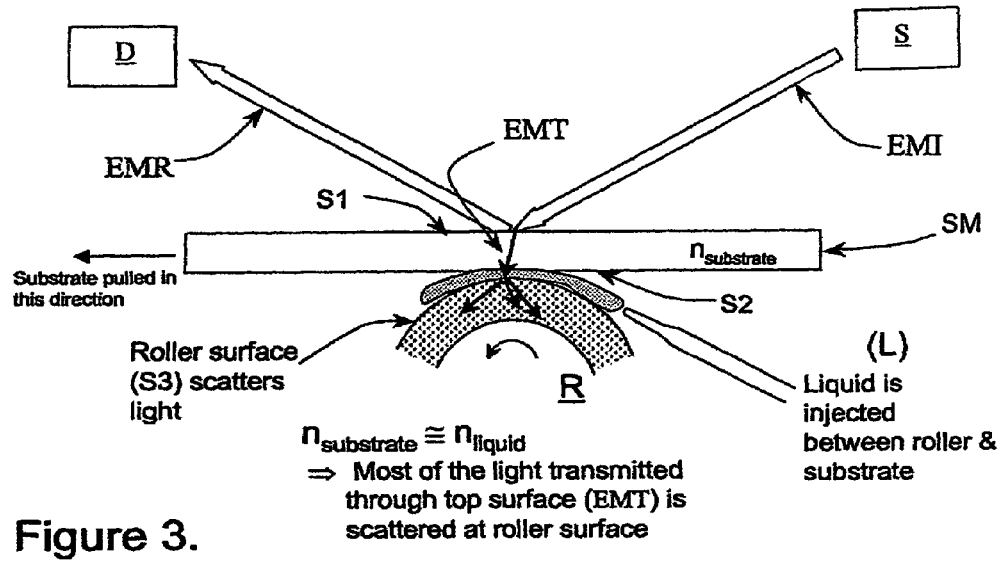
FIGS. 3 and 4 demonstrate present invention systems components for supporting a sample, including means to reduce back side reflections comprising an index matching liquid between said components for supporting a sample and a sample, such that backside reflections are reduced when the samples are investigated by thereby.
Figure 4:
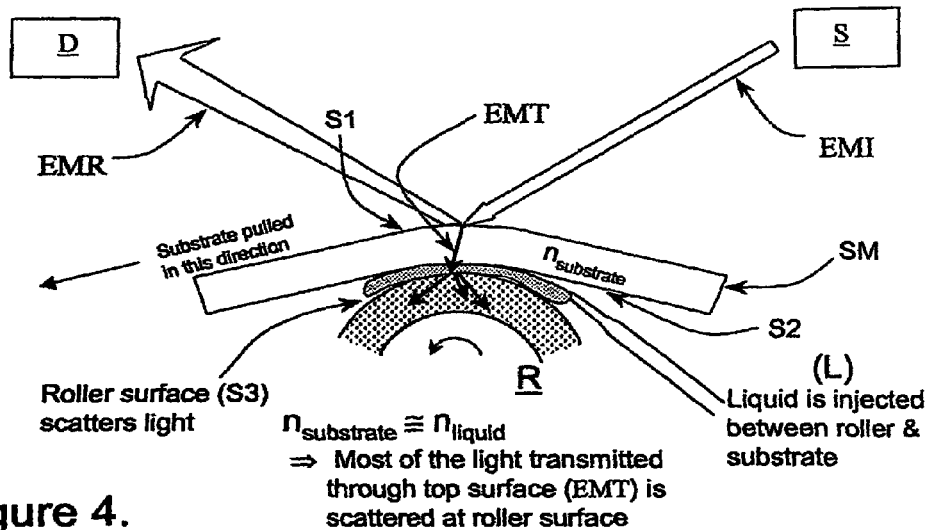

Said means for supporting (R) and said sample (SM) can each be rigid, (see FIGS. 1 and 3 which show a rigid sample), or deformable, (see FIGS. 2 and 4 which show a deformable sample).

A method of monitoring reflections of electromagnetic radiation caused to impinge on the surface of a sample (SM) at an oblique or normal angle of incidence, while substantially preventing backside reflections therefrom from complicating the results, comprising the steps of:

a) providing a system comprising:

a sample (SM);

a means for supporting (R) a sample (SM);

a source (PSG) of a beam (EMI) of electromagnetic radiation; and a detector (PSD) of said beam (EMR) of electromagnetic radiation;

wherein said means for supporting (R) a sample (SM) is present under said sample (SM) near the location thereof whereat, during use, a beam (EMI) of electromagnetic radiation provided by said source (PSG) thereof is caused to impinge thereupon at an oblique or normal angle of incidence;

said means for supporting (R) a sample and said sample being characterized by a selection from the group consisting of:
    having substantially matched indices of refraction; and
    having liquid (L) present at the interface therebetween which is substantially index matched to that of said sample (SM);
  b) causing said source (PSG) of a beam of electromagnetic radiation to provide a beam (EMI) of electromagnetic radiation to impinge on a surface of said sample (SM), at an oblique or normal angle of incidence;
  c) monitoring electromagnetic radiation reflected (EMR) from said sample (SM) surface which enters said detector (PSD).

Said method can be practiced where with a means for supporting a sample is deformable or rigid and/or where the sample is deformable or rigid.

It is also to be understood that the (PSG) and (PSD) in FIGS. 1-4 can be rotated in position about a normal to the sample (SM) through 0-360 degrees so that the plane formed thereby is oriented as shown, or in any such rotated position. That is, for instance, if the sample is elongated, the beam of electromagnetic radiation provided by said source thereof which is caused to impinge thereupon at an oblique or normal angle of incidence; can be directed along a locus which is selected from the group consisting of:
    parallel to the elongated dimension of said sample;
    perpendicular to the elongated dimension of said sample;
    between parallel and perpendicular to the elongated dimension of said sample.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

I claim:

1. A system comprising:
   a sample;
   a means for supporting said sample;
   a source of a beam of electromagnetic radiation; and
   a detector of electromagnetic radiation;
wherein said means for supporting said sample is present under said sample near the location of said sample whereat, during use, a beam of electromagnetic radiation provided by said source of a beam of electromagnetic radiation is caused to impinge at an oblique or normal angle of incidence, reflect therefrom, and enter said detector of electromagnetic radiation;
said means for supporting a sample and said sample being characterized by a selection from the group consisting of:
   having essentially matched indices of refraction; and
   having liquid present at the interface therebetween which is substantially index matched to that of said sample.

2. A system as in claim 1, wherein said means for supporting a sample is rigid.

3. A system as in claim 1, wherein said means for supporting a sample is deformable.

4. A system as in claim 1, wherein said sample is rigid.

5. A system as in claim 1, wherein said sample is flexible.

6. A system as in claim 1 which further comprises liquid between said sample and said means for supporting a sample, said liquid being substantially refractive index matched to said sample.

7. A system as in claim 1, wherein the sample is elongated and the beam of electromagnetic radiation provided by said source thereof which is caused to impinge thereupon at an oblique or normal angle of incidence; is directed along a locus which is selected from the group consisting of:
   parallel to the elongated dimension of said sample;
   perpendicular to the elongated dimension of said sample;
   between parallel and perpendicular to the elongated dimension of said sample.

8. A method of monitoring reflections of electromagnetic radiation caused to impinge on the surface of a sample at an oblique or normal angle of incidence, while substantially preventing backside reflections from complicating the results, comprising the steps of:
   a) providing a system comprising:
      a sample;
      a means for supporting said sample;
      a source of a beam of electromagnetic radiation; and
      a detector of electromagnetic radiation;
wherein said means for supporting said sample is present under said sample near the location of said sample whereat, during use, a beam of electromagnetic radiation provided by said source of a beam of electromagnetic radiation is caused to impinge thereupon at an oblique or normal angle of incidence, reflect therefrom, and enter said detector of electromagnetic radiation;
said means for supporting a sample and said sample being characterized by a selection from the group consisting of:
   having substantially matched indices of refraction; and
   having liquid present at the interface therebetween which is substantially index matched to that of said sample;
   b) causing said source of a beam of electromagnetic radiation to provide a beam of electromagnetic radiation which impinges on a surface of said sample, at an oblique or normal angle of incidence;
   c) monitoring electromagnetic radiation reflected from said sample surface which enters said detector;
said method being characterized by at least one selection from the group consisting of:
   storing at least some data provided by said data detector in machine readable media;
   analyzing at least some of the data provided by said detector of electromagnetic radiation and storing at least some of the results of said analysis in machine readable media;
   displaying at least some data provided by said detector of electromagnetic radiation by electronic and/or non-electronic means;
   analyzing at least some of the data provided by said detector of electromagnetic radiation and displaying at least some of the results of said analysis by electronic and/or non-electronic means;
   causing at least some data provided by said detector of electromagnetic radiation to produce a signal which is applied to provide a concrete and tangible result;
   analyzing at least some of the data provided by said detector of electromagnetic radiation and causing at least some thereof to produce a signal which is applied to provide a concrete and tangible result.

9. A method as in claim 8, wherein said sample is a sheet or ribbon and is caused to move over said means for supporting a sample while said reflected electromagnetic radiation from said sample surface enters said detector.

10. A method as in claim 9 wherein said step of providing a sample involves providing a sample that is flexible.

11. A method as in claim 9 wherein said step of providing a sample involves providing a sample that is rigid.

12. A method as in claim 9 wherein said step of providing a means for supporting a sample involves providing a means which is rigid.

13. A method as in claim 9 wherein said step of providing a means for supporting a sample involves providing a means which is deformable.

14. A method as in claim 8, wherein the sample is elongated and the beam of electromagnetic radiation provided by said source thereof which is caused to impinge thereupon at an oblique or normal angle of incidence; is directed along a locus which is selected from the group consisting of:
   parallel to the elongated dimension of said sample;
   perpendicular to the elongated dimension of said sample;
   between parallel and perpendicular to the elongated dimension of said sample.

15. A method of monitoring reflections of electromagnetic radiation caused to impinge on the surface of a sample at an oblique or normal angle of incidence, while substantially preventing backside reflections from complicating the results, comprising the steps of:
   a) providing a system comprising:
      a sample which is of an elongated sheet or ribbon shape;
      a means for supporting said sample;
      a means for causing said sample to move over said means for supporting a sample;
      a source of a beam of electromagnetic radiation; and
      a detector of electromagnetic radiation;
   wherein said means for supporting said sample is present under said sample near the location of said sample whereat, during use, a beam of electromagnetic radiation provided by said source of a beam of electromagnetic radiation is caused to impinge thereupon at an oblique or normal angle of incidence, reflect therefrom, and enter said detector of electromagnetic radiation;
   said means for supporting a sample and said sample being characterized by a selection from the group consisting of:
      having substantially matched indices of refraction; and
      having liquid present at the interface therebetween which is substantially index matched to that of said sample;
   b) causing said source of a beam of electromagnetic radiation to provide a beam of electromagnetic radiation which impinges on a surface of said sample, at an oblique or normal angle of incidence;
   c) while causing said means for causing said sample to move over said means for supporting a sample to move said sample over said means for supporting a sample, monitoring electromagnetic radiation reflected from said sample surface which enters said detector of electromagnetic radiation;
   said method being characterized by at least one selection from the group consisting of:
      storing at least some data provided by said data detector of electromagnetic radiation in machine readable media;
      analyzing at least some of the data provided by said data detector of electromagnetic radiation and storing at least some of the results of said analysis in machine readable media;
      displaying at least some data provided by said data detector of electromagnetic radiation by electronic and/or non-electronic means;
      analyzing at least some of the data provided by said data detector of electromagnetic radiation and displaying at least some of the results of said analysis by electronic and/or non-electronic means;
      causing at least some data provided by said data detector of electromagnetic radiation to produce a signal which is applied to provide a concrete and tangible result;
      analyzing at least some of the data provided by said data detector of electromagnetic radiation and causing at least some thereof to produce a signal which is applied to provide a concrete and tangible result.

16. A method as in claim 15 wherein said step of providing a sample involves providing a sample that is flexible.

17. A method as in claim 15 wherein said step of providing a sample involves providing a sample that is rigid.

18. A method as in claim 15 wherein said step of providing a means for supporting a sample involves providing a means which is rigid.

19. A method as in claim 15 wherein said step of providing a means for supporting a sample involves providing a means which is deformable.

20. A method as in claim 15, wherein the sample is elongated and the beam of electromagnetic radiation provided by said source thereof which is caused to impinge thereupon at an oblique or normal angle of incidence; is directed along a locus which is selected from the group consisting of:
   parallel to the elongated dimension of said sample;
   perpendicular to the elongated dimension of said sample;
   between parallel and perpendicular to the elongated dimension of said sample.

* * * * *